US009861569B2

(12) United States Patent
Brujic et al.

(10) Patent No.: US 9,861,569 B2
(45) Date of Patent: Jan. 9, 2018

(54) SPECIFICITY, FLEXIBILITY AND VALENCE OF DNA BONDS FOR GUIDED EMULSION ARCHITECTURE

(71) Applicant: New York University, New York, NY (US)

(72) Inventors: Jasna Brujic, New York, NY (US); Lang Feng, Jersey City, NJ (US); Lea-Laetitia Pontani, New York, NY (US); Paul Chaikin, Pennington, NJ (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/266,026

(22) Filed: Apr. 30, 2014

(65) Prior Publication Data

US 2014/0330002 A1     Nov. 6, 2014

Related U.S. Application Data

(60) Provisional application No. 61/854,769, filed on May 1, 2013.

(51) Int. Cl.
| | |
|---|---|
| C07H 21/04 | (2006.01) |
| A61K 8/64 | (2006.01) |
| A61Q 19/00 | (2006.01) |
| A61K 8/02 | (2006.01) |
| A23L 29/10 | (2016.01) |
| A23L 35/00 | (2016.01) |

(52) U.S. Cl.
CPC ............ *A61K 8/64* (2013.01); *A23L 29/10* (2016.08); *A23L 35/10* (2016.08); *A61K 8/0241* (2013.01); *A61Q 19/00* (2013.01); *A61K 2800/413* (2013.01); *A61K 2800/57* (2013.01)

(58) Field of Classification Search
CPC ... A23L 1/035; A23L 1/483; A61K 2800/413; A61K 2800/57; A61K 8/0241; A61K 8/64; A61Q 19/00
USPC .................. 536/23.1, 25.3; 424/450, 490
See application file for complete search history.

(56) References Cited

U.S. PATENT DOCUMENTS

| | | | |
|---|---|---|---|
| 6,645,528 | B1 | 11/2003 | Straub et al. |
| 7,785,617 | B2 | 8/2010 | Shakesheff et al. |
| 8,315,821 | B2 | 11/2012 | Brujic |
| 2004/0258248 | A1 | 12/2004 | Schnitta et al. |
| 2005/0174238 | A1 | 8/2005 | Foseide |
| 2006/0078624 | A1 | 4/2006 | Zalipsky et al. |
| 2008/0045156 | A1 | 2/2008 | Sakhpara |
| 2009/0098272 | A1* | 4/2009 | Banken ............... A23L 1/30 426/590 |
| 2009/0275465 | A1* | 11/2009 | Gang ................. C12Q 1/6816 502/159 |
| 2012/0214001 | A1 | 8/2012 | Little et al. |
| 2012/0224706 | A1 | 9/2012 | Hwang et al. |
| 2012/0250581 | A1 | 10/2012 | Bilcu et al. |
| 2013/0236416 | A1 | 9/2013 | Rungta et al. |
| 2014/0161270 | A1 | 6/2014 | Peters et al. |
| 2015/0134418 | A1 | 5/2015 | Leow et al. |
| 2015/0245139 | A1 | 8/2015 | Park |

FOREIGN PATENT DOCUMENTS

WO     WO-2013/150349 A1     10/2013

OTHER PUBLICATIONS

Hadorn et al. PNAS | Dec. 11, 2012 | vol. 109 | No. 50, 20320.*
Pontani et al. PNAS | Jun. 19, 2012 | vol. 109 | No. 25 | 9839-9844.*
Final Office Action on U.S. Appl. No. 13/889,083 dated Apr. 4, 2016, 9 pages.
Adams, Cynthia L., et al., "Mechanisms of Epithelial Cell-Cell Adhesion and Cell Compaction Revealed by High-resolution Tracking of E-Cadherin-Green Flourescent Protein", The Journal of Cell Biology, vol. 142, No. 4, Aug. 24, 1998, pp. 1105-1119.
Alexander, S., "Amorphous Solids: Their Structure, Lattice Dynamics and Elasticity", *Physics Reports*, (1998), pp. 65-236, vol. 296, Elsevier Science B.V.
Angres, Brigitte, et al., "Mechanism for Transition from Initial to Stable Cell-Cell Adhesion: Kinetic Analysis of E-Cadherin-Mediated Adhesion Using a Quantitative Adhesion Assay", The Journal of Cell Biology, vol. 134, No. 2, Jul. 1996, pp. 549-557.
Anishchik et al., "Three Dimensional Apollonian Packing as a Model for Dense Granular Systems", *Physical Review Letters*, Dec. 4, 1995, pp. 4314-4317, vol. 75, No. 23, The American Physical Society, USA.
Asakura et al., "Interaction between Particles Suspended in Solutions of Macromolecules". *Journal of Polymer Science*, (1958), pp. 183-192, vol. 33.
Aste et al., "An invariant distribution in static granular media", *EPL*, Jul. 2007, pp. 24003-p1--24003-p5, vol. 79, www. epljournal.org.
Aste et al., "Emergence of Gamma distributions in granular materials and packing models", *Physical Review E*, (2008), pp. 021309-1--021309-8, vol. 77.
Atilgan, Erdinc et al., "Nucleation and Growth of Integrin Adhesions", Biophysical Journal, vol. 96, May 2009, pp. 3555-3572.
Basan, Markus, et al., "Dissipative particle dynamics simulations for biological tissues: reheology and competition", Phys. Biol. 8 (2001) pp. 1-13.
Bell, George I., "Models for the Specific Adhesion of Cells to Cells", Science vol. 200, May 12, 1978, pp. 618-627.
Bibette et al., "Depletion Interactions and Fluid-Solid Equilibrium in Emulsions", *Physical Review Letters*, Nov. 5, 1990, pp. 2470-2473, vol. 65, No. 19, The American Physical Society, USA.
Bibette et al., "Emulsions: basic principles", *Rep., Prog. Phys.*, (1999), pp. 969-1033, vol. 62, IOP Publishing Ltd., UK.
Bibette et al., "Kinetically Induced Ordering in Gelation of Emulsions", *Physical Review Letters*, Aug. 10, 1992, pp. 981-984, vol. 69, No. 6, The American Physical Society.

(Continued)

*Primary Examiner* — Janet L Epps-Smith
(74) *Attorney, Agent, or Firm* — Foley & Lardner LLP

(57) ABSTRACT

A method of forming an end product by self-assembly of a first component having a patch of a linker component, such as DNA strands, cadherins, adhesive proteins and nanoparticle linkers. Such emulsions can be used to process personal care products, skin cremes, foods and animal feedstocks.

14 Claims, 10 Drawing Sheets

(56) References Cited

OTHER PUBLICATIONS

Borghi, Nicolas, et al., "Regulation of cell motile behavior by crosstalk between cadherin- and integrin-mediated adhesions", PNAS, Jul. 27, 2010, vol. 107, No. 30, pp. 13324-13329.
Bourouina, Nadia, et al., "Formation of Specific receptor-ligand bonds between liquid interfaces", The Royal Society of Chemistry 2001, Soft Matter, 2011, 7, pp. 9130-9139.
Bruinsma, Robijn et al., "Adhesive switching of membranes: Experiment and theory", Physical Review E. vol. 61, No. 4., Apr. 2000, pp. 4253-4267.
Brujić, J., "Experimental Study of Stress Transmission Through Particulate Matter", *A Dissertation submitted for the degree of Doctor of Philosophy at the University of Cambridge*, Feb. 2004, 202 pages, University of Cambridge Cavendish Laboratory.
Brujic, Jasna et al., "3D bulk measurements of the force distribution in a compressed emulsion system", The Royal Society of Chemistry 2003, pp. 207-220.
Brujic, Jasna, "Measuring the Coordination Number of Entropy of a 3D Jammed Emulsion Packing by Confocal Microscopy", Physical Review Letters, Jun. 15, 2007, pp. 248001-248004.
Chen, Chien Peter et al., "Specificity of cell-cell adhesion by classical cadherins: Critical role for low-affinity dimerization through β-strand swapping", www.pnas.org/cgi/doi/10.1073/onas.0503319102, PNAS, Jun. 14, 2004, vol. 102, No. 24, pp. 8531-8536.
Chu, Yeh-Shiu, et al., "Force Measurements in E-cadherin-mediated cell doublets reveal rapid adhesion strengthened by actin cytoskeleton remodeling through Rac and Cdc42", The Journal of Cell Biology, Vo. 167, No. 6, Dec. 20, 2004, pp. 1183-1194.
Clusel et al., "A 'granocentric' model for random packing of jammed emulsions", Nature, Jul. 30, 2009, pp. 611-616, vol. 460, Macmillan Publishers Limited.
Crocker et al., "Entropic Attraction and Repulsion in Binary Colloids Probed with a Line Optical Tweezer", *Physical Review Letters*, May 24, 1999, pp. 4352-4355, vol. 82, No. 21, The American Physical Society, USA.
Cuvelier, Damien et al., "Hidden Dynamics of Vesicle Adhesion Induced by Specific Stickers", Physical Review Letters, Nov. 26, 2004, pp. 228101-1 to 228101-4.
Danisch et al., "Model of random packings of different size balls", *Physical Review E.*, (2010), pp. 051303-1--051303-5, vol. 81, The American Physical Society, USA.
Douezan, Stephane, et al., "Spreading dynamics and wetting transition of cellular aggregates", PNAS, May 3, 2011, vol. 108, No. 18, pp. 7315-7320.
Du Roure, O., et al., "Homophilic Interactions between Cadherin Fragments at the Single Molecule Level: An AFM Study", Langmuir, vol. 11, No. 10, 2006, pp. 4680 to 4684.
Fasolo et al., "Effects of colloid polydisperity on the phase behavior of colloid-polymer mixtures", *The Journal of Chemical Physics*, (2005), pp. 074904-1--074904-13, vol. 122, American Institute of Physics, USA.
Fattaccioli, Jacques et al., "Specific wetting probed with biomimetic emulsion droplets", www.rsc.org/softmatter, Soft Matter, 2008, vol. 4., pp. 2434,2440.
Finney, J. L., "Random packings and the structure of simple liquids I. The geometry of random close packing", *Proc. Roy. Soc. Lond. A.*, Nov. 10, 1970, pp. 479-493, vol. 319, No. 1539, The Royal Society.
Foty, Ramsey A., "Surface tensions of embryonic tissues predict their mutual development behavior", The Company of Biologists Limited 1996, Development 122, pp. 1611-1620 (1996).
Foty, Ramsey A., "The differential adhesion hypothesis: a direct evaluation", Development Biology, 278 (2005), pp. 255-263.
Guevorkian, Karien et al., "Aspiration of Biological Viscoelastic Drops", Physical Review Letters, vol. 104, May 28, 2010, pp. 218101-1 to 218101-4.
Helmlinger, Gabriel, "Solid stress inhibits the growth of multicellular tumor spheroids", Nature Biotechnology, vol. 15, Aug. 1997, pp. 778-783.
Henkes et al., "Statistical mechanics framework for static granular matter", *Physical Review E.*, (2009), pp. 061301-1--061301-20, vol. 79, The American Physical Society, USA.
Jaoshvili et al., "Experiments on the Random Packing of Tetrahedral Dice", *Physical Review Letters*, (2010), pp. 185501-1--185501-4, vol. 104, The American Physical Society, USA.
Katgert et al., "Jamming and geometry of two-dimensional foams", *EPL-A Letters Journal! Exploring the Frontiers of Physics*, (2010), pp. 34002-p1--34002-p8, vol. 92, www.epljournal.,org.
Kurita et al., "Experimental study of random-close-packed colloidal particles", *Physical Review E*, (2010), pp. 011403-1--011403-9, vol. 82, The American Physical Society, USA.
Ladoux, Benoit et al., "Strength Dependence of Cadherin-Mediated Adhesions", Biophysical Journal, vol. 98, Feb. 2010, pp. 534-542.
Lechenault et al., "Free volume distributions and compactivity measurement in a bidimensional granular packing", *Journal of Statistical Mechanics: Theory and Experiment*, (2006), pp. 1-16, IOP Publishing Ltd and SISSA.
Lee et al., "Formation and evolution of sediment layers in an aggregating colloidal suspension", *Physical Review E*, (2006), pp. 031401-1--031401-11, vol. 74, The American Physical Society, USA.
Liu, Zhijun, et al., "Mechanical tugging force regulates the size of cell-cell junctions", PNAS, Jun. 1, 2010, vol. 107, No. 22, pp. 9944-9949.
Lu et al., "Gelation of particles with short-range attraction", *Nature*, May 22, 2008, pp. 499-504, vol. 453, Nature Publishing Group.
Mahaffy, R.E., "Scanning Probe-Based Frequency-Dependent Microrheology of Polymer Gels and Biological Cells", Physical Review Letters, Jul. 24, 2000, vol. 85, No. 4, pp. 880-883.
Majmudar et al., "Jamming Transition in Granular Systems", *Physical Review Letters*, (2007), pp. 58001-1--58001-4, vol. 98, The American Physical Society, USA.
Man et al., "Experiments on Random Packings of Ellipsoids", *Physical Review Letters*, (2005), pp. 198001-1--198001-4, vol. 94, The American Physical Society, USA.
Manning, Lisa N., "Coaction of intercellular adhesion and cortical tension specifies tissue surface tension", PNAS, Jul. 13, 2010, vol. 107, No. 28, pp. 12517-12522.
Mason et al., "Elasticity of Compressed Emulsions", *Physical Review Letters*, Sep. 4, 1995, pp. 2051-2054, vol. 75, No. 10, The American Physical Society.
Mehta et al., "Statistical Mechanics of Powder Mixtures", *Physica A*, (1989), pp. 1091-1100, vol. 157, Elsevier Science Publishers B.V., (North-Holland Physics Publishing Division).
Nowak et al., "Reversibility and irreversibility in the packing of vibrated granular material", *Powder Technology*, (1997), pp. 79-83, vol. 94, Elsevier Science S.A.
O'Hern et al., "Force Distributions near Jamming and Glass Transitions", *Physical Review Letters*, Jan. 1, 2001, pp. 111-114, vol. 86, No. 1, The American Physical Society, USA.
Panorchan, Porntula, "Single-molecule analysis of cadherin-mediated cell-cell adhesion", Journal of Cell Science 119, Sep. 28, 2005, pp. 66-74.
Papusheva, Ekaterina, et al., "Spatial Organization of adhesion: force-dependent regulation and function in tissue morphogenesis", The EMBO Journal, vol. 29, No. 16, 2010, pp. 2753-2768.
Pautot, Sophie et al., "Engineering Asymmetric Vesicles", PNAS, Sep. 16, 2003, vol. 100, No. 19, pp. 10718-10721.
Perez-Moreno, Mirna et al., "Sticky Business: Orchestrating Cellular Signals at Adherens Junctions", Cell, vol. 112, Feb. 21, 2003, pp. 535-548.
Pham et al., "Glasses in hard spheres with short-range attraction", *Physical Review E*, (2004), pp. 011503-1--011503-13, vol. 69, The American Physical Society, USA.
Sackmann, Erich, et al., "Cell Adhesion as Wetting Transition?", ChemPhysChem, 2002, vol. 3, pp. 262-269.
Scott, G. David, "Packing of Spheres", Nature, Dec. 10, 1960, pp. 908-909, vol. 188, Nature Publishing Company.
Song et al., "A phase diagram for jammed matter", *Nature*, May 29, 2008, pp. 629-632, vol. 453, Nature Publishing Group.

(56) References Cited

OTHER PUBLICATIONS

Song et al., "Experimental measurement of an effective temperature for jammed granular materials", *PNAS*, Feb. 15, 2005, pp. 2299-2304, vol. 102, No. 7, www.pnas.org.

Sperl, M., "Dynamics in colloidal liquids near a crossing of glass- and gel-transition lines", *Physical Review E.*, (2004), pp. 011401-1--011401-13, vol. 69, The American Physical Society, USA.

Tambe T. Dhananjay et al., "Collective cell guidance by cooperative intercellular forces", Nature Materials, vol. 10, Jun. 2011, pp. 469-475.

Thiery, Jean Paul et al., "Complex networks orchestrate epithelial-mensenchymal transitions", Molecular Cell Biology, vol. 7, Feb. 2006, pp. 131-142.

Thiery, Jean Paul, "Cell adhesion in development: a complex signaling network", Current Opinion in Genetics & Development 2003, vol. 13, pp. 365-371.

Torquato et al., "Is Random Close Packing of Spheres Well Defined", *Physical Review Letters*, Mar. 6, 2000, pp. 2064-2067, vol. 84, No. 10, The American Physical Society, USA.

Vasioukhin, Valeri et al., "Directed Actin Polymerization Is the Driving Force for Epithelial Cell-Cell Adhesion", Cell, vol. 100, Jan. 21, 2000, pp. 209-219.

Walker, Scott A., et al., "Controlled Multi-Stage Self-Assembly of Vesicles", Matt. Res. Soc, Symp. Proce., vol. 372, 1995, pp. 95-100.

Yap, Alpha S., et al., "Direct cadherin-activated cell signaling: a view from the plasma membrane", The Journal of Cell Biology, vol. 160, No. 1, Jan. 6, 2003, pp. 11-16.

Yuan, Chunbo et al., "Energy Landscape of Streptavidin—Biotin Complexes Measured by Atomic Force Microscopy", Biochemistry 2000, vol. 39, pp. 10219-10223.

Zou et al., "The Packing of Granular Polymer Chains", *Science*, Oct. 16, 2009, pp. 408-410, vol. 326, www.sciencemag.com.

Breed, Dana Rachel, "Engineered Colloids: Patchy Particles with Reversible, Directional Interactions", University of California Santa Barbara dissertation, Dec. 2007, 175 pages.

Kraft, D., et al., "Surface roughness directed self-assembly of patchy particles into colloidal micelles", PNAS, Jul. 3, 2012, 109(27):15 pages.

Pine, David, "Colloidal Self Assembly II: Pacmen & Multivalent Colloids",2012 Boulder Summer School, Jul. 25, 2012, Boulder Colorado, 46 pages.

International Search Report and Written Opinion in PCT/US2013/067051, dated Mar. 6, 2014, 7 pages.

Non-Final Office Action in U.S. Appl. No. 14/629,312, dated Apr. 7, 2016, 14 pages.

Final Office Action in U.S. Appl. No. 14/629,312, dated Oct. 24, 2016, 11 pages.

Notice of Allowance in U.S. Appl. No. 14/629,312, dated Jan. 19, 2017, 10 pages.

Non-Final Office Action in U.S. Appl. No. 13/889,083, dated Mar. 7, 2017, 9 pages.

\* cited by examiner

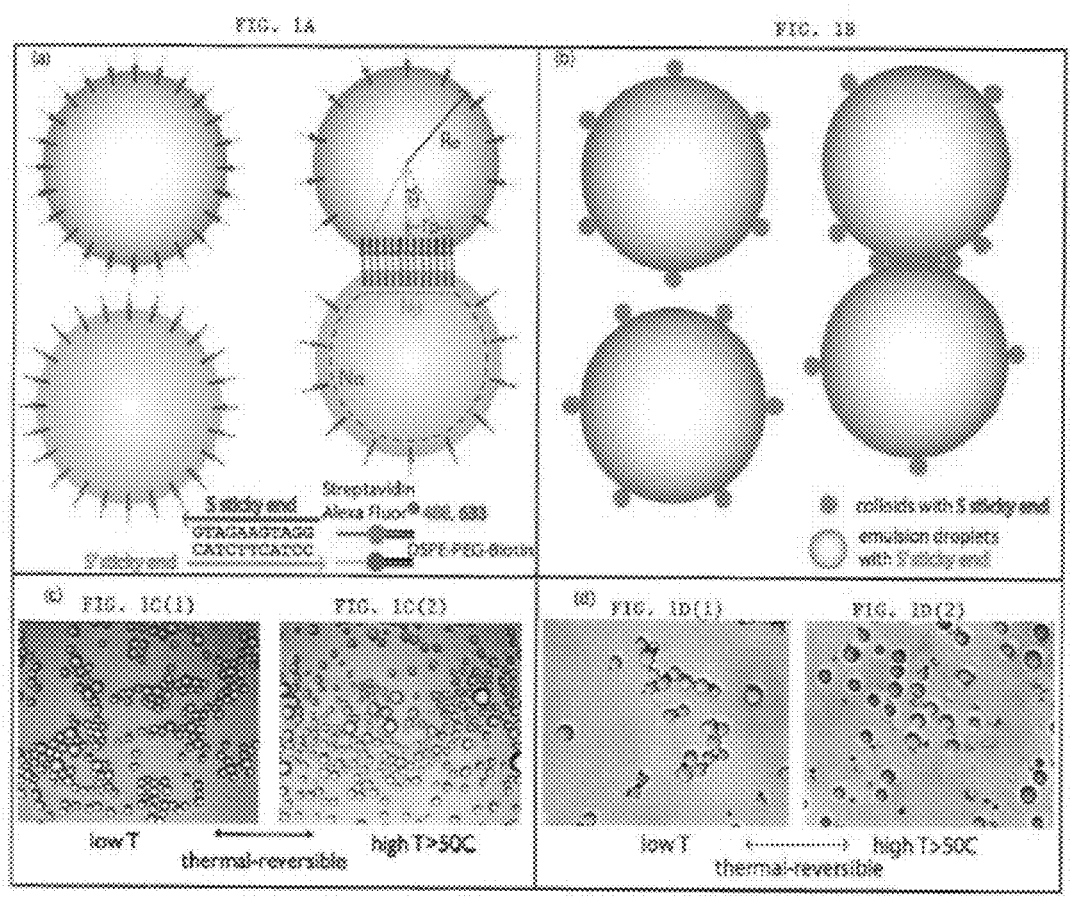

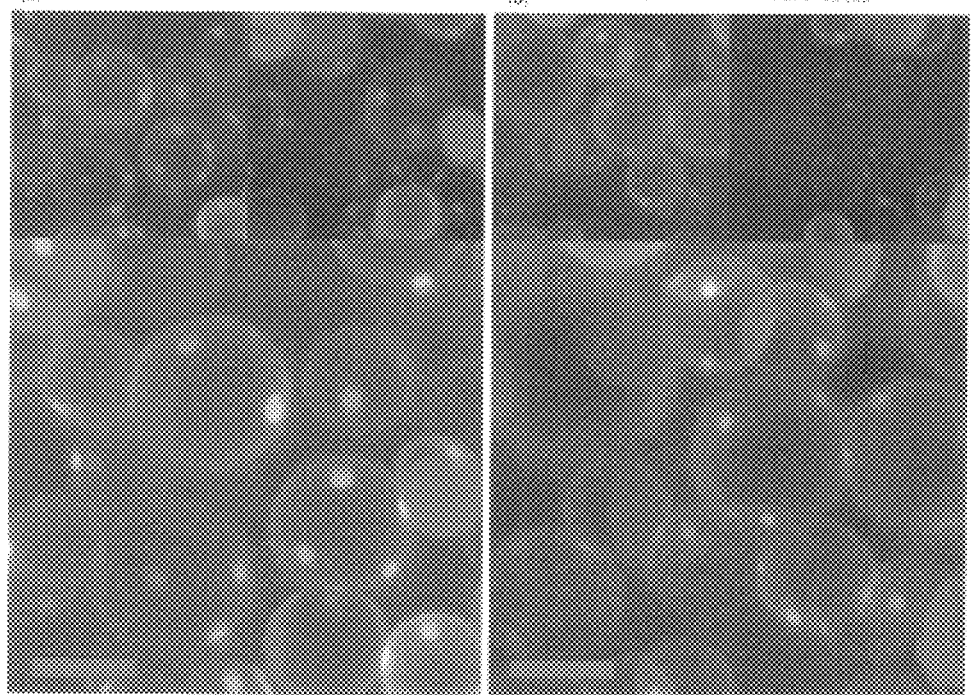

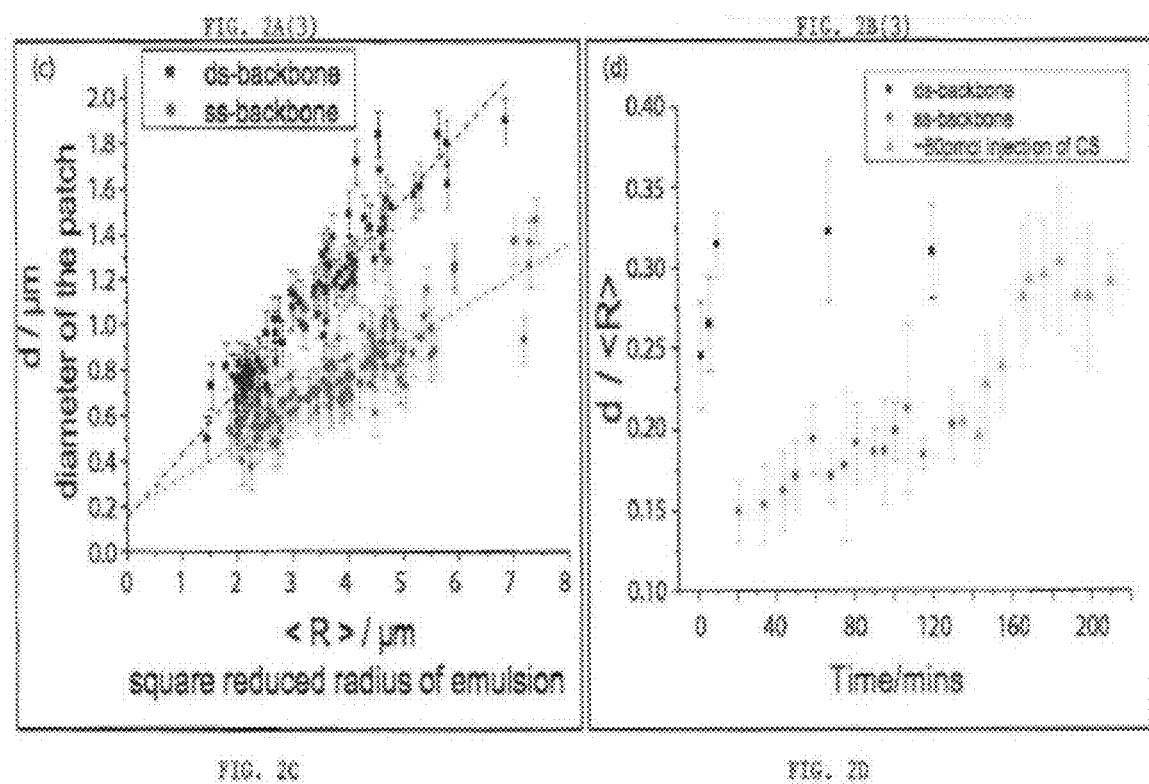

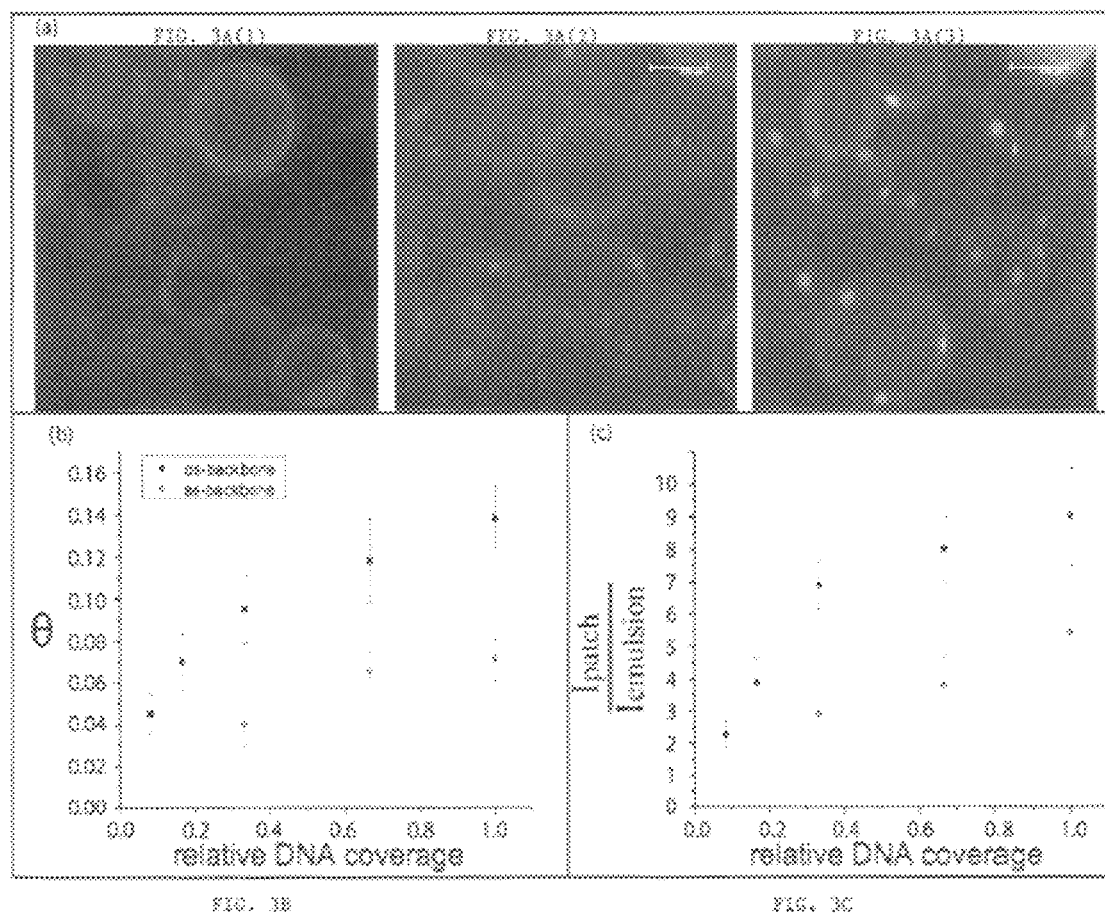

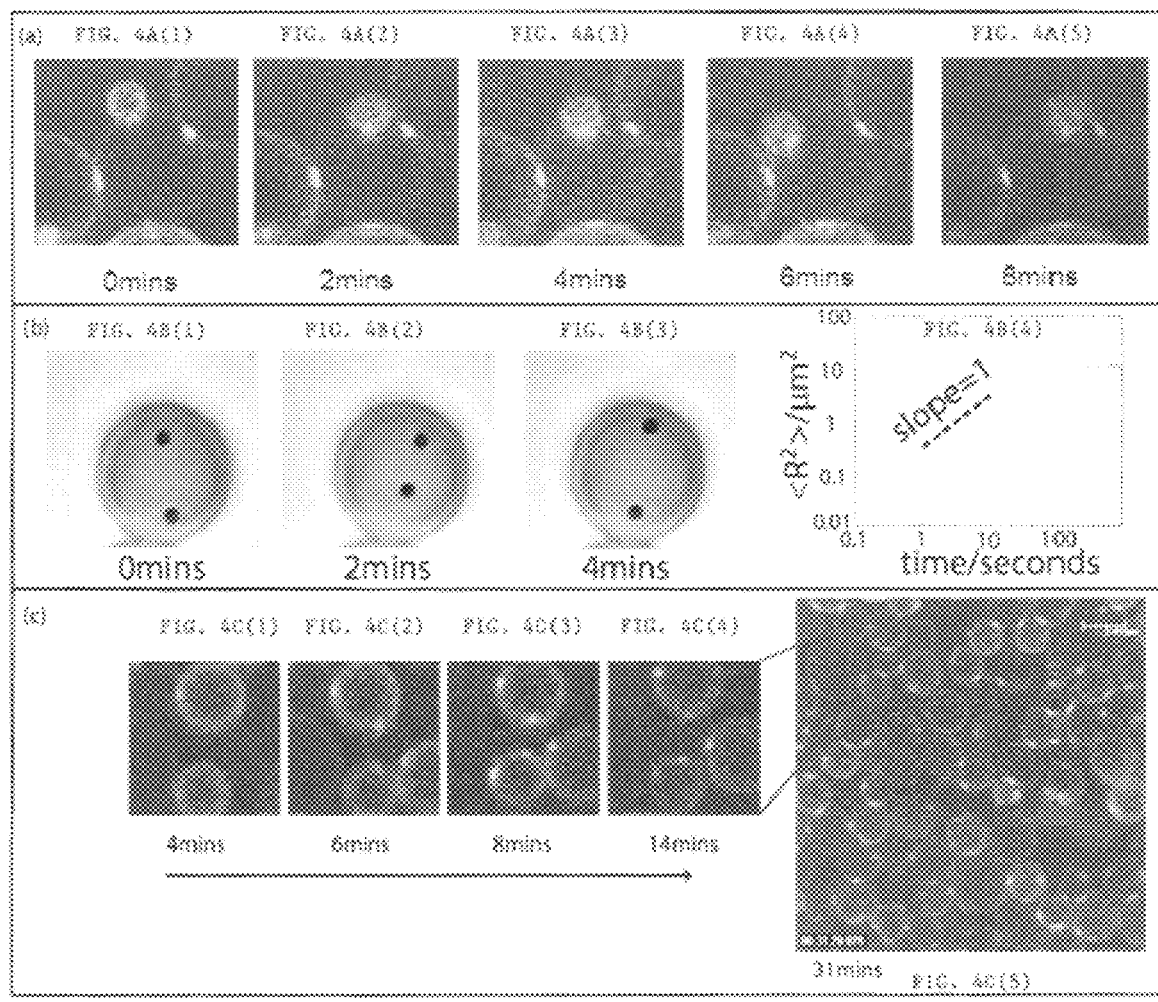

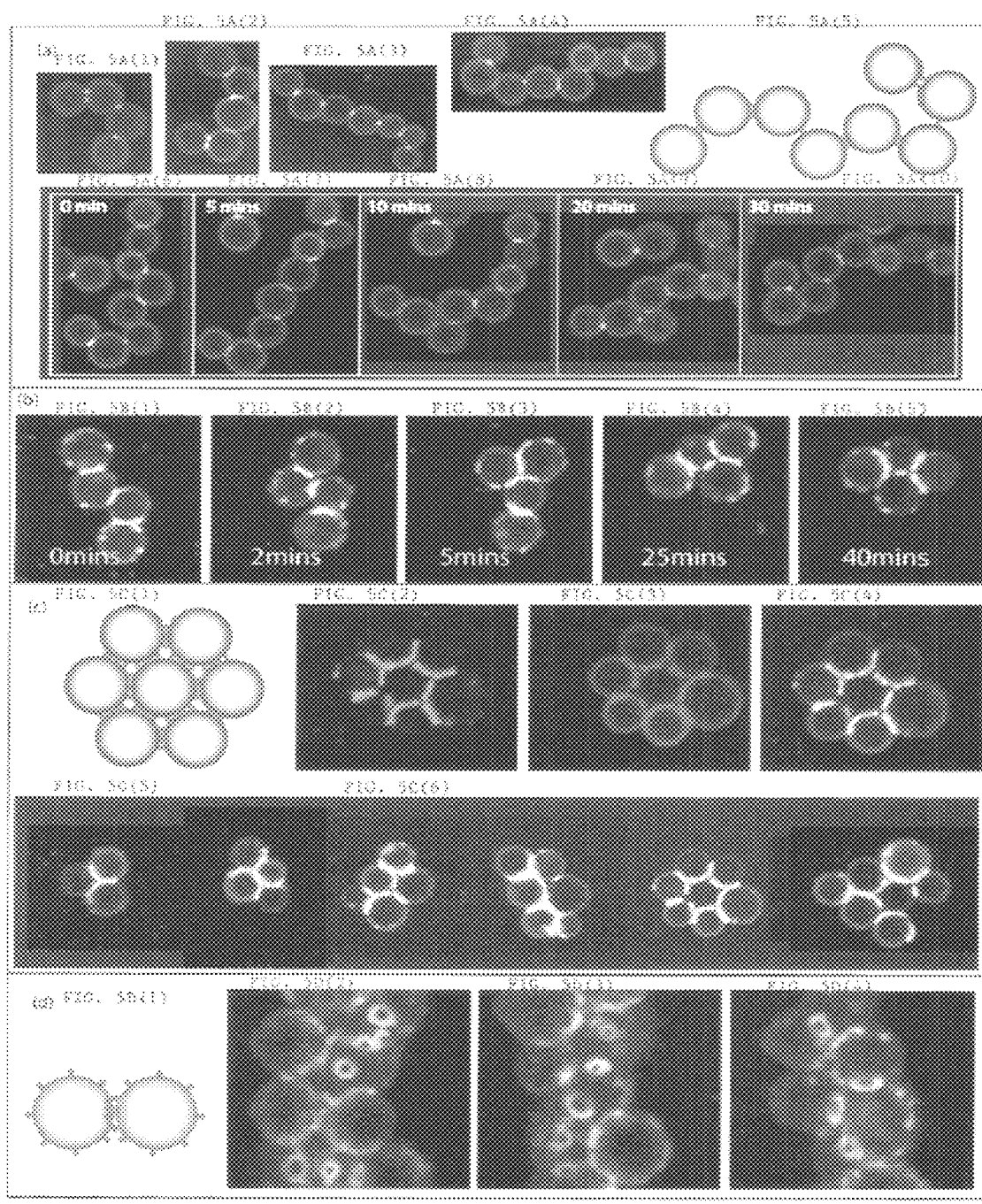

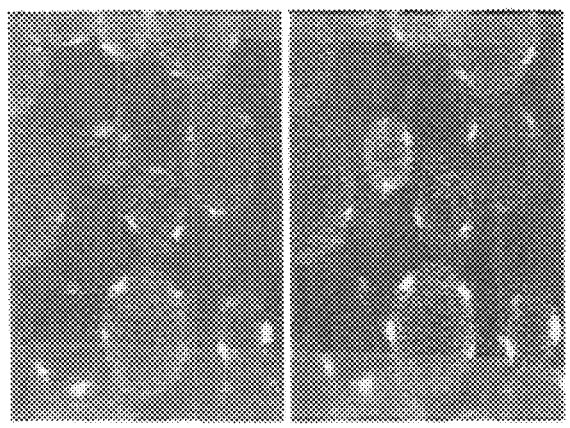
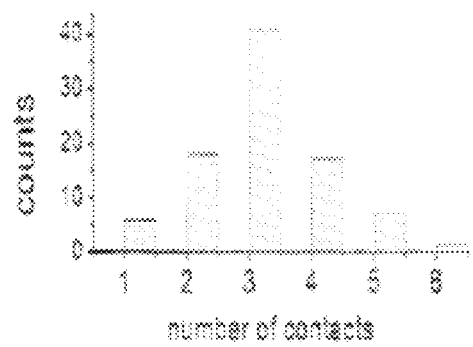
FIG. 9a
FIG. 9b

SPECIFICITY, FLEXIBILITY AND VALENCE OF DNA BONDS FOR GUIDED EMULSION ARCHITECTURE

CROSS REFERENCE TO RELATED APPLICATIONS

This applications claims priority to U.S. Provisional Application No. 61/854,769 filed May 1, 2013, which is hereby incorporated by reference in its entirety.

STATEMENT OF GOVERNMENT RIGHTS

The U.S. Government has certain rights in this invention pursuant to support under the MRSEC Program of the National Science Foundation under Grant No. DMR-0820341 and the National Science Foundation Career Grant No. 0955621.

SEQUENCE LISTING

The instant application contains a Sequence Listing which has been submitted electronically in ASCII format and is hereby incorporated by reference in its entirety. Said ASCII copy, created on May 30, 2014, is named 046434-0453_SL.txt and is 1,779 bytes in size.

FIELD OF THE INVENTION

This invention is directed to the self-assembly and directed controlled assembly of complex particle architectures. More particularly this invention is directed to methods, system and product materials employing DNA component sequences, cadherins, other adhesive proteins on cell membranes and solid nanoparticles serving as droplet linkers to construct a wide range of particle assemblages and architectures.

BACKGROUND OF THE INVENTION

Self-assembly of particles is of great interest for the design of complex particulate architectures to create smart nano-materials with tunable optical, mechanical or electronic properties. Grafting linking components, onto liquid interfaces of emulsions can lead to new architectural possibilities. In one example of particle linking components, the specific and programmable interaction between complementary DNA components has been used to assemble colloidal molecules with specific symmetries imposed by the positions of the grafted DNA.

Consequently it is desirable to further expand the application of selected linking components to improve formulation of particle architectures and create new systems for various applications.

SUMMARY OF THE INVENTION

In one preferred embodiment DNA interactions have been developed to establish that the size and number of these adhesion patches (valency) can be controlled. Valence values of 2 lead to flexible polymers of emulsion droplets, while valence values above 4 lead to rigid droplet networks. In one example, a simple thermodynamic model quantitatively describes the increase in the patch size with droplet radii, DNA concentration and the stiffness of the tether to the sticky-end. The patches are formed between droplets with complementary DNA strands or alternatively with complementary colloidal nanoparticles to mediate DNA binding between droplets. This emulsion system opens the route to directed self-assembly of more complex structures through distinct DNA bonds with varying strengths and controlled valence and flexibility.

DNA strands can be grafted onto thermal oil-in-water emulsions. Mixing two emulsions with complementary DNA strands leads to their specific binding through strong yet reversible adhesion patches. Unlike solid colloidal particles, liquid droplets are able to rearrange within the packed structure once they are bound together. Moreover, the deformation of the emulsion droplets, i.e. the size of the adhesion patch, provides a direct probe of the free energy of binding. A thermodynamic model has been developed to relate the adhesion size to the binding free energy and discover that the entropy loss upon binding plays an important role. The validity of the model has been tested by varying the DNA surface density the stiffness of the tether and the droplet size. This system sheds light on the mechanisms of adhesion between contacting liquid surfaces. Emulsion self-assembly leads to segregated floppy networks, which are amorphous materials with advantageous rheological properties. In addition, it has been determined that colloidal nanoparticles can serve as mediators of the DNA interaction between droplets. Controlling their concentration determines the valence of the droplets and enables us to uniquely create linear emulsion strings or those that fold into compact clusters. Consequently, this system and method provides a highly advantageous tool for self-assembly and controlled or directed applications.

In other embodiments cadherins, other adhesive proteins on cell membranes and selected nanoparticles can also be used to establish controlled self-assembly linkages. A variety of commercial applications are possible for these embodiments, such as personal care products, skin creams, foods and feedstocks for animals.

The foregoing summary is illustrative only and is not intended to be in any way limiting. In addition to the illustrative aspects, embodiments, and features described above, further aspects, embodiments, and features will become apparent by reference to the following drawings and the detailed description. These and other objects, advantages and features of the invention and related claims herein, together with the organization and manner of operation therefore, will become apparent from the following detailed description where taken in conjunction with the accompanying drawings wherein like elements have like numerals throughout the several drawings described below.

BRIEF DESCRIPTION OF THE DRAWINGS

FIG. 1A illustrates an adhesive DNA-emulsion system wherein silicone oil droplets are stabilized with phospholipids, some of which are labeled with fluorescently dyed streptavidin that allow the grafting of S or S' DNA strands; S functionalized emulsion is dyed in green ("g") while the S' one is dyed in red ("r"); complementary S and S' sticky ends (SEQ ID NOS 4 and 5, respectively) then bind and form adhesion patches enriched in DNA tethers between the droplets; in FIG. 1B colloids are coated with the S DNA strand and dyed in green ("g") which can stick to S' functionalized droplets and eventually bridge to droplets together through a colloidal patch; FIGS. 1C(1) and 1C(2) are for a temperature below the DNA melting temperature Tm=50° C. and the complementary thermal droplets aggregate into clusters (FIG. 1C(1)) that are disrupted above the Tm (FIG. 1C(2)); and FIGS. 1D(1) and 1D(2) similarly show the S coated particles only stick to the complementary S' emulsion below Tm (see FIG. 1D(1)) to form large composite structures of multiple droplets linked through particles and those clusters as well as individual droplet-particle interactions dissociate above Tm (see FIG. 1D(2));

FIGS. 2A(1)-A(3) illustrate entropy-dependent adhesion patches between complementary emulsions with confocal imaging of S (green or "g") and S' (red or "r") complementary emulsions interaction reveal the formation of adhesion patches for double stranded (dsb); FIGS. 2B(1)-B(3) are a single stranded (ssb) construct; and FIG. 2C shows diameter of the patch as a function of the squared radius <R> for two interacting droplets of radii $R_1$ and $R_2$ for dsb (squares) and ssb DNA (circles), with $$\langle R \rangle = \sqrt{\frac{2R_1^2 R_2^2}{R_1^2 + R_2^2}};$$

Figure 6:
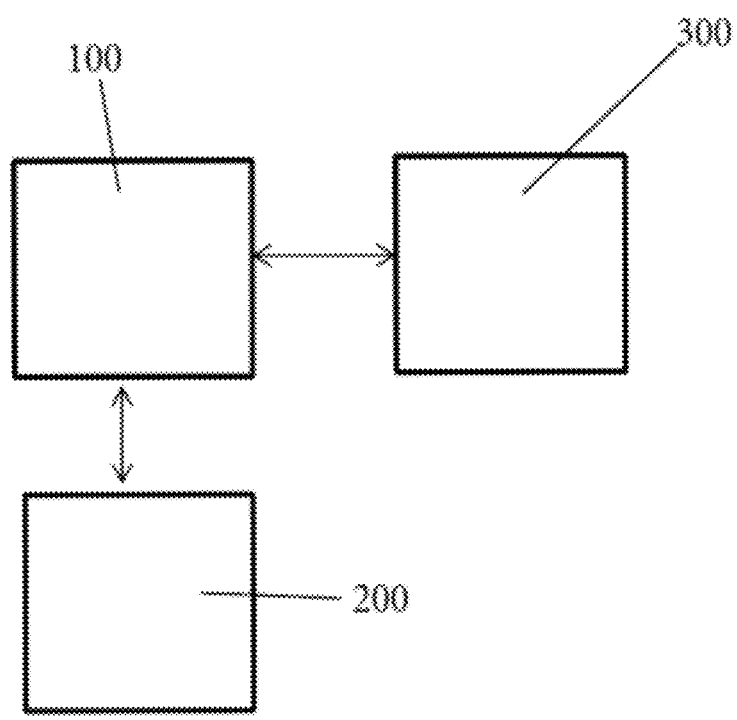
Figure 7:
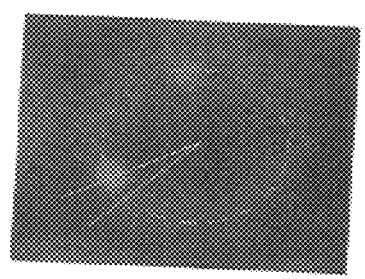
Figure 8:
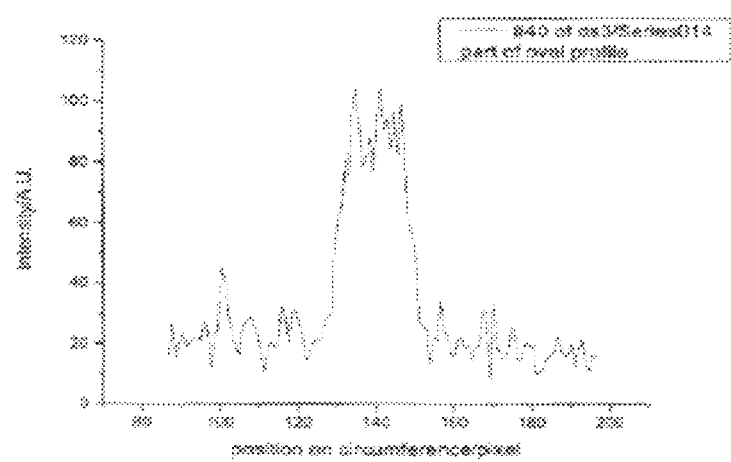

data are fitted by the model (dashed lines) on FIG. 2D; growth of the patch size (diameter/<R>) is plotted as a function of time for dsb (squares) and ssb (circles) DNA; and triangles record the growth of ssb patches after addition of complementary strands, which turn into dsb patches after ~40 min;

FIGS. 3A(1)-3A(3) illustrate dependence of patch size and intensity on DNA coverage, showing confocal images of the adhesion patches between complementary droplets for increasing DNA coverages on the droplets surface (DNA coverage from left to right: FIG. 3A(1) shows ~17% (middle); FIG. 3A(2) shows ~34% (right); and FIG. 3A(3) shows 100% which is ~1400 strands/$\mu m^2$; FIG. 3B shows patch angle θ and FIG. 3C shows relative intensity plotted as a function of the relative DNA coverage on the droplets and the experimental data are well fitted by the model (solid lines);

FIGS. 4A(1)-4C(4) show diffusivity of complementary bonds, wherein FIGS. 4A(1)-4A(5) show green emulsion droplet diffusing on a complementary droplet along with the adhesion patch; FIGS. 4B(1)-4B(3) show two S coated particles bound to a S' coated droplet diffuse on its surface; FIG. 4B(4) shows the mean square displacement of the particles with time reveals a diffusive behavior with a diffusion coefficient D=0.012 $\mu m^2/s$ on the surface of phospholipid stabilized emulsions; and FIGS. 4C(1)-4C(5) show an emulsion network connected by specific DNA bonds;

FIGS. 5A(1)-5D(4) illustrate self-assembly of the colloid-emulsion system, wherein FIGS. 5A(1)-A(4) in particular show micrographs of various configurations, FIG. 5A(5) shows a schematic chain, and FIGS. 5A(6)-5A(10) show layer formations of polymer chains; polymer chains of emulsion droplets are stabilized by two adhesion patches formed using complementary nanoparticles; and the divalent emulsion droplets result from a low nanoparticle/droplet ratio ~5; FIGS. 5B(1)-5B(5) show that at higher nanoparticle/droplet ratios more than two adhesion patches can form over time, leading in this case to a trivalent 20 structure; FIG. 5C(1) shows a schematic and 5C(2)-5C(5) show large particle/droplet ratios, ~100, can produce multivalent droplets and lead to compact rigid structures in which the beads (green or "g") all assemble between the droplets (red or "r") contacts to minimize the system's energy, and FIG. 5D(1) shows a schematic polymer and FIGS. 5D(2)-5D(4) show time lapse formation of the colloidal nanoparticles assembling as rings between droplet contacts to maximize the amount of droplet/particle adhesive area with little droplet deformation;

FIG. 6 illustrates a block schematic diagram of a computer system to carry out determination of various products and associated models for creating selected chemical architecture of the invention;

FIG. 7 illustrates confocal imaging of the adhesion patches between the droplets. The fluorescence intensity along the droplets surface is analyzed with the Oval Profile plugin in image 7. Once the patch is identified from the circular intensity profile (see next figure), the fluorescence intensity along two radii inside the outside of the patch are also measured for contrast measurements;

FIG. 8 illustrates oval profile along the circumference of a droplet. The central plateau has an average intensity of (can this be moved down to be level with the line?) $I_{patch}+I_{noise}=88\pm9$ AU. We define the width of the peak as the diameter of the patch, which is here of 20 pixels or $d_{patch}=$ (please move down so level on line) 1.2 μm. The average intensity in the peripheral region is the background noise estimated from the droplets central intensity is evaluated to be $I_{noise}=9.8\pm3$ AU. Averaging this among different slices significantly reduces the error bar. Assuming that the concentration of streptavidin is linearly proportional to the measured fluorescence intensity, the streptavidin enrichment in the patch is $$\frac{C_{patch}}{C_{emulsion}} = \frac{I_{patch}}{I_{emulsion}} = 7.5.$$

Figure 10:
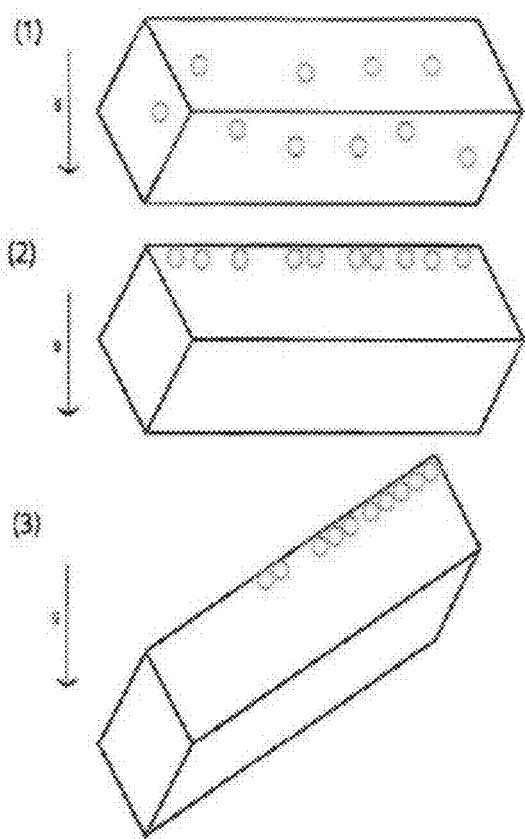

This value as well as $d_{patch}$ are used in the main text in FIGS. 8 and 9, using statistics from different slices, patches and droplets;

FIG. 9a illustrates the bonds between complementary red and green emulsions are mobile, even after the structure reaches the maximum droplet connectivity (left). The distribution of the number of red-green sticky contacts can be measured with many confocal scan (see FIG. 9b); and FIG. 10 illustrates development of emulsion polymeric chains beginning with a dilute suspension of S' coated emulsion droplets is mixed with the complementary S coated particles top a ratio of particle/droplet ~5%. The capillary is first tilted horizontally to force the creaming of the droplets in the top corner. The droplets are then brought together by an additional slight vertical tilting that makes them slide together and adhere through the particles to form emulsion polymeric chains.

DETAILED DESCRIPTION OF PREFERRED EMBODIMENTS

Various methods and chemical components were implemented and are described herein to illustrate details of preferred embodiments. A number of "valence" values were used to control size and architecture development for product materials. These advantageous features and attributes will be illustrated by the following description and examples.

A model emulsion system using DNA as an example linker system is shown in FIG. 1A and is stabilized with a mixture of two phospholipids, Egg-Phosphatidylcholine (EPC) and PEG-biotinylated lipids, and a small amount of a conventional SDS surfactant. The biotinylated lipids are saturated with fluorescent streptavidin, which in turn binds to a second biotin from the functional DNA strand. The green emulsion (Alexa Fluor 488® streptavidin) is coated with the S sequence, while the red emulsion (Alexa Fluor 633® streptavidin) is coated with the S' sequence (see Example section). In addition to the complementary sticky ends, the binders have an identical backbone of either single stranded or double stranded DNA that serves as a tether to the binder. Alternatively, we study a hybrid system of interacting colloidal nanoparticles and emulsions, as illustrated in FIG. 1B. In this system the emulsion is only decorated with the S' DNA sequence (red or "r"), which interacts with colloids coated with the complementary S sequence (green or "g"). As a result, a colloidal particle binds droplets together.

The thermal reversibility of DNA interactions in these systems allows switching the adhesion between droplets on and off by cycling the temperature above and below the DNA melting temperature of $T_m = 50°$ C. At room temperature, complementary emulsions are mixed together and diffuse to form adhesive clusters (see FIG. 1C(1)) that dissociate upon heating above $T_m$ (see FIG. 1C(2)). Similarly, the emulsion-colloid system below $T_m$ reveals multivalent particle-emulsion structures (see FIG. 1D(1)) that are separated upon heating (see FIG. 1D(2)).

When complementary droplets meet, their DNA strands hybridize to form double-stranded (ds) DNA. Therefore, the presence of green and red streptavidin, associated with each DNA strand, lead to yellow adhesion patches in regions of hybridization, as shown in FIGS. 2A(1)-2A(3) (dsb) and FIGS. 2B(1)-B(3) (ssb). The patches in emulsions with double stranded backbone (dsb) tethers are significantly larger than those with single stranded backbone (ssb) tethers. In both cases, the plot of the patch size as a function of the reduced radius of each pair of contacting droplets in FIG. 2C reveals a linear dependence. Thus, the measured ratio of dsb to ssb patch sizes of ~1.6 is independent of droplet size. This result indicates that the strength of binding between droplets can be modulated in situ by adding the complementary strand to ssb functionalized emulsions. The patch size is observed to transition from the average size expected for ssb DNA interactions to the ~1.6 times larger adhesions corresponding to dsb DNA in less than one hour, as shown in FIG. 2D.

Another way to increase the binding strength, as well as the number of patches per droplet, is to increase the DNA coverage on the droplets, C, as shown in the 3D perspective images in FIGS. 3A(1) and A(3). The patch size (θ) and the relative intensity, defined as the ratio of the intensity of fluorescence in the patch and that of the droplet surface, increase as a function of DNA coverage in FIGS. 3B and C. This capability allows one to tune the reversibility of droplet interactions and the temperature at which the structures melt.

In one preferred embodiment a model of the experimental observation is implemented by a statistical mechanic model. It is based on the assumption that binders are recruited into the contact area until the binding energy balances the energy cost upon droplet deformation and the entropy penalty due to the immobilization of the DNA tether in the patch. Consider two complementary emulsion droplets with the same radius Re and DNA surface density $N_0/(4R_e^2)$, where $N_0$ is the total number of DNA on the droplet. The two droplets interact to form an adhesive patch of radius $r_p$ and deformation angle $\theta = r_p/R$, as shown in FIG. 1A. $N_\beta$ is the number of DNA binders inside the patch between two complementary droplets, and $N_\alpha$ the amount of free DNA strands remaining on the droplet surface. The global free energy change from the unbound to the bound state is then:

$$\Delta F = \Delta E_{DNA,\beta} - 2T(S_\beta + S_\alpha) + E_{deform} - F_{unbound} \quad (1)$$

where $E_{dna}$ is the binding energy, T is the temperature, S is the entropy of binding and $E_{deform}$ is the energy cost to deform the interface. Subscripts β and α indicate the binding patch region and the unbound surface, respectively. In the dilute case, $S_\beta = -kN_\beta \ln[C_\beta/C_0]$ where $C_\beta = N_\beta/\pi r_p^2$ is the surface density of DNA in the adhesive patch and $C_0$ is the reference concentration, which cancels out in the calculation. The binding free energy for the mobile DNA patch is estimated in mean field: $\Delta E_{DNA,\beta} = N_\beta[\Delta G_{DNA} - T\Delta S_r - k_B T \ln(A_w C_\beta)]$, where $\Delta G_{DNA}$ is the free energy of hybridization of free DNA in solution, $\Delta S_r$ is the entropy loss due to rotational constraints of hybridized DNA strands at low temperature, $A_w$ the area in which two DNA strands can move relative to each other when hybridized and $\ln(A_w C_\beta)$ is the translational entropy penalty for two DNA strands bound in the patch. The deformation energy is given by $E_{deform} = \sigma \pi R_e^2 \theta^4/2$, where σ is the surface tension. Since there are only two independent parameters in the problem, $C_\beta$ and $r_p$, the global energy is minimized to obtain the profile of $C_\beta(C_\alpha, A_w)$ and $\theta(C_\alpha, A_w)$:

$$\theta(C_\alpha, A_w) = r_p/R_e = \left[\frac{kT[-2\ln(1 - C_\beta A_{strep}) - C_\beta A_{strep}]}{\sigma A_{strep}}\right]^{1/2} \quad (2)$$

assuming that the binding free energy $\Delta G_{DNA}$, the surface tension σ, the streptavidin size $A_{strep}$ and the temperature T are kept constant. Since the double stranded tether is much longer and can reach as far as ~26 nm, further than that of the single stranded tether of ~4.5 nm, the area of relative motion of bound DNA strands, $A_w$, is also much larger, estimated to be ~2000 nm² compared to only ~60 nm². Therefore, the dsb case loses less entropy upon binding which quantitatively explains the ~1.6 fold larger average patch size, as shown in FIG. 2C. Moreover, the adhesion strength dependence is captured on the DNA surface coverage with only two fitting parameters: the rotational entropy loss $\Delta S_r = 16R$ (where R is the gas constant) and the maximum DNA binding capability, N=12 pmol, for an emulsion sample of 30 µL. These fitting parameters are consistent with previously reported values. The agreement of the model with the experimental data for the three trends shown in FIG. 2C and FIGS. 3B and 3C illustrate validity of the model enabling further exploitation of that model for advantageous methods and systems.

The fluidity of the droplet surface enables rearrangements in bound structures and allows for the self-assembly of programmable geometries. Adhesion patches are free to diffuse despite the high binding energy of ~20000 DNA connections in an average-sized patch with a 1.6 µm diameter. FIGS. 4A(1)-A(5) show the diffusion of droplets that are bound through DNA interactions, but free to rotate with respect to each other and thus enable exploring available configurations. A hybrid system of particles and emulsions is used to quantify the diffusion of adhesion patches (see FIGS. 4B(1)-B(4)). The beads serve as reporters for the lipid motion on the monolayer surface. To measure relative motion, two colloidal particles coated with the S DNA sequence are attached onto the surface of a S' functionalized droplet through at least 200 DNA bonds. The mean square displacement of one bead with respect to the other (see FIG. 4B(4)) yields a diffusion constant of D~0.012 µm²/s. This value is significantly smaller than both the diffusion of a single lipid of size ~1 nm in a fluid model membrane with $D$~1-10 $\mu m^2/s$ [27-30] and that of a 1 μm colloidal particle with $D_{particle}$~0.5 $\mu m^2/s$. This slow diffusion of the particle is due to the strong hydrodynamic drag of an adhesive lipid patch of radius ~100 nm, which is expected to be two orders of magnitude lower than that of a single lipid.

Allowing the emulsions to cream to the surface assembles floppy networks of bound droplets that are organized by the specificity of the DNA bonds, as shown in FIGS. 4C(1)-C (5). Once the maximum droplet connectivity is achieved, no further rearrangements in the structure are observed. Nevertheless, the bonds continue to be mobile owing to the liquid interfaces. While the coordination number distribution of such networks can be tuned by the concentration of binders on the surface, their structure remains amorphous.

Alternatively, the complementary colloid-emulsion hybrid system, as shown in FIG. 1B, can be used as a versatile tool for self and directed-assembly. Combining the dilute emulsion (~1000 droplet/mm$^2$) with complementary nanoparticles at a low particle/droplet ratio of ~5 enables the formation of linear emulsion polymers of different lengths, as shown in FIGS. 5A(1)-A(10). The linear arrangement of the droplets is induced by constraining them in a 1-D line at the edge of a tilted rectangular capillary. The binding colloids are recruited exclusively to the emulsion contacts after overnight incubation to form two patches per emulsion droplet and thus prevent branching. This leads to polymer chains with a valency of two that diffuse over time due to the mobility of the particulate joints between the droplets. They remain in a linear configuration because the particles are too small to bridge three droplets. On the other hand, at a higher particle/droplet ratio of ~100 we observe multivalency and folding of the linear chains into compact structures over time, as shown in FIGS. 5B(1)-B(5). In that case, the binding energy of the multivalent particles and their connectivity is sufficient to arrest the resulting structure. The geometry of the final compact structure depends on the valency, the number of droplets in the cluster, as well as the kinetic pathway, and ranges from triangular lattices to flowers, as shown in FIG. 5C(1)-C(6). These structures lower their energy by maximizing the number of colloids that occupy emulsion contacts. Unlike droplet-droplet patches, shown in FIGS. 2A(1)-2b(3), 3a(1)-a(3) and 4a(1)-a(5) and C(1)-C (5), the solid polystyrene particles are large enough to bridge two emulsion droplets without reaching their contact point. This leads to a ring structure in the adhesion zone, as shown in the confocal images of clusters in FIGS. 5D(1)-D(4). The circular arrangements maximizes the number of particles per emulsion contact and thereby minimizes the global free energy.

Self-assembly of thermal emulsion polymer chains can be achieved with programmable droplet interactions using DNA interactions, cadherins and selected nanoparticles. Controlling the number of binders and the length of the chain one can obtain divalent, trivalent and multivalent structures. In addition, the mobility of adhesive patches within these structures allows them to evolve into geometries that are governed by the underlying free energy landscape. Furthermore, such interactions allow one to program the shape of the free energy landscape through the control of bond specificity, strength, flexibility and valency. This system promises to become a highly advantageous system and method for producing products by directed self-assembly because it has the potential of building intelligently designed materials, such as colloidal crystals or artificial self-replicating materials, with no external inputs.

These materials and methods can be used for a variety of commercial applications including, without limitation, controlled formation of personal care products, food processing, skin creams, pharmaceutical products, foods and animal feedstocks.

Various embodiments are described in the general context of method steps, which may be implemented in one embodiment by a computer 100 having an embedded program in a non-transitory storage medium 200 and including computer-executable instructions, such as program code, executed by the computer 100 in networked environments or in the cloud 300. In FIG. 6 is shown a block diagram illustrating such a system. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

The following non-limiting Examples illustrate selected aspects of the invention.

EXAMPLE I

Synthesis of Biomimetic Emulsion:
The protocol for the emulsion preparation is a conventional, well known methodology. The oil droplets are stabilized with egg L-α-phosphatidylcholine (EPC) lipids and the DSPE-PEG(2000) biotinylated lipids from Avanti Polar Lipids at a molar ratio of 92:8, respectively. After cooling to room temperature the lipid containing oil (10 mL) can be emulsified in two different buffers to reach different droplet sizes. Athermal droplets are obtained when emulsified in a buffer containing 5 mMSDS and $w_t$=18% dextran and sheared at 22 rpm in the narrow gap coquette mixer. Smaller droplets sizes are obtained with a buffer containing 5 mMSDS and $w_t$=4.5% alginate and a shearing rate of 30 rpm. The resulting emulsions are stable over several weeks at 4° C.

DNA coated emulsion preparation: The emulsion is first coated with two different fluorescent streptavidins: Alexa Fluor 488® and Alexa Fluor 633® streptavidin (Molecular Probes). 100 μL of emulsion is mixed with 10 μL of 1 mg/mL streptavidin and 300 μL of buffer containing 2 mM Tris pH=7 and 1 mM SDS. The solution is incubated 1 h at 4° C. and then washed twice with the same buffer, before a final wash in the DNA buffer (1 mM SDS, 5 mM PBS, 4 mM MgCl2). The DNA can then be added to the streptavidin coated emulsion: 10 μL of 50 μM DNA is added to the solution and incubated 1 h at room temperature. The remaining unbound DNA is finally washed three times in the DNA buffer. One type of fluorescent streptavidin is specifically associated with one DNA strand in order to distinguish them by microscopy.

DNA Constructs:

The S strand has a sequence: 5'-BiotinTEG-49bp backbone-GGATGAAGATG-3' (SEQ ID NO: 1);

The S' strand has a sequence: 5'-BiotinTEG-49bp backbone-CATCTTCATCC-3" (SEQ ID NO: 2);

The CS strand complementary to the backbone: 5'-TCG TAA TGA AAG GCA GGG CTC TCT GGA TTG ACT GTG CGAAGG GTA GCG AT-3" (SEQ ID NO: 3)

TEG: Tetra-Ethylene Glycol

Confocal microscope: The samples are imaged using a fast scanning confocal microscope (Leica TCS SPS 11).

Light microscope with a temperature stage: A Leica DMRXA microscope with Qimaging Retiga 1300 camera is used to obtain microscopic images. A temperature stage is built on the light microscope to provide fast in-situ temperature control. Briefly, $1000\Omega$ ITO glass is placed on a 3 mm thick copper plate, two ends of which are connected to peltiers (2.5 cm by 2.5 cm) then to a thermal sink with constant temperature. With LakeShore DRC 93C Temperature Controller and LakeShore PT-111 temperature sensor, we are able to control and detect the temperature with <0.5° C. relative error.

EXAMPLE II

Consider two interacting droplets of the same radius R and coated with complementary strands of DN, when two DNA strands from opposite surfaces bind together, they gain binding energy but lose entropy due to the spatial constraint into the patch. The system also endures a deformation energy cost to allow the droplets to deform and form the adhesion patch area.

First we use the simple 'lattice model' (or 'box model') to get the entropy of molecules in a non-dilute solution. Given the total area $S_{total}$, the molecule (streptavidin) size $A_{strep}$, the number of streptavidins N and the total number of sites available on the droplet surface $N_0 = S_{total} A_{strep}$ where (move down to be on same line)

$$N_0 = \frac{S_{total}}{A_{strep}},$$

the total number of configurations reads:

$$\Omega = \frac{N_0!}{(N_0 - N)! N!} \quad (3)$$

Using the Stirling's formula the entropy is approximated to:

$$S = k\ln(\Omega) = k\left[N\ln\left(\frac{N_0 - N}{N}\right) + N_0\ln\left(\frac{N_0}{N_0 - N}\right)\right] \quad (4)$$

With the binding energy for a pair of DNA sticky ends (move down on same line) $\Delta G_{DNA} = \Delta F_{DNA} - T\Delta S_{DNA}$, the deformation energy of the droplet [2] and the entropy term derived in Equation (2), we can write down the global free energy difference between the bound state and the non-interacting droplets state as follows:

$$\Delta F = E_{DNA,\beta} - 2(TS_\beta + TS_\alpha) + E_{deformation} - F_{unbound} \quad (5)$$

The subscript β refers to the adhesive patch region while α refers to the non-interacting region on the rest of the droplet surface. Since two droplets interact to form a patch, the entropy term has to be taken into account twice which justifies the prefactor.

The energy terms in Equation (3) can be written:

$$E_{DNA,\beta} = -kT \ln\left[\left(1 + \exp\left(-\frac{\Delta G_{DNA} - T\Delta S_r - T\ln(A_w C_\beta)}{kT}\right)\right)^{N_\alpha} - 1\right] \quad (6)$$

The entropy and the deformation energy in Equation (3) can be written:

$$S_\beta = k\left[N_\beta \ln\left(\frac{N_{\beta 0} - N_\beta}{N_\beta}\right) + N_{\beta 0}\ln\left(\frac{N_{\beta 0}}{N_{\beta 0} - N_\beta}\right)\right] \quad (7)$$

$$S_\alpha = k\left[N_\alpha \ln\left(\frac{N_{\alpha 0} - N_\alpha}{N_\alpha}\right) + N_{\alpha 0}\ln\left(\frac{N_{\alpha 0}}{N_{\alpha 0} - N_\alpha}\right)\right]$$

$$E_{deformation} = \frac{1}{2}\sigma\pi R^2 \theta^4 = \frac{1}{2}\sigma\pi \frac{r_p^4}{R^2}$$

Where $r_p$ is the radius of the enriched patch; θ is defined as the deformation angle $r_p/R$; σ is the surface tension of the emulsion; $N_- + N_- = N$ gives the total number of streptavidins, $N_\beta$ of them being in the binding patch; (try to move all these inserts to be level with line) $N_{\alpha\theta} + N_{\beta\theta} = N_\theta = 4\pi R^2 / A_{strep}$ gives the total number of biotin sites on a emulsion, while $N_{\beta\theta} = \pi r_p^2 / A_{strep}$ is the number of sites available in the patch area; $C_\beta = N_\beta / (\pi r_p^2)$ is the concentration of streptavidin in the patch; $A_w$ is the area over which two bound DNA strands could move relative to each other while remaining hybridized; $\Delta S_r$ and $k \ln(A_w C_\beta)$ are the configurational entropy lost due to rotational and translational confinement of hybridized DNA sticky ends, respectively.

We now minimize this global free energy ΔF with respect to two independent parameters in the equations: $N_{\beta\theta}$ and $N_\beta$. Note that we could conversely use the two independent parameters $C_\beta$ and $r_p$ instead, which would result in the same equations.

The first equation leads to the chemical potential equilibrium. In the strong binding case where $\Delta F_{DNA} - T\Delta S_{DNA} - T\Delta S_r$ at least a few kT, this first equation can be simplified as follows:

$$\Delta G_{DNA} - T\Delta S_r - kT - kT \ln(A_w C_\beta) \quad (8)$$
$$- 2T\left[k\ln\left(\frac{N_{\beta 0} - N_\beta}{N_\beta}\right) - k\ln\left(\frac{N_{\alpha 0} - N_\alpha}{N_\alpha}\right)\right] = 0$$

The second equation reads:

$$kT\frac{N_\beta}{N_{\beta 0}} - 2kT\left[\ln\left(\frac{N_{\beta 0}}{N_{\beta 0} - N_\beta}\right) - \ln\left(\frac{N_{\alpha 0}}{N_{\alpha 0} - N_\alpha}\right)\right] + \frac{\sigma N_{\beta 0} A_{strep}^2}{\pi R^2} = 0 \quad (9)$$

The resulting $N_\beta$ and $N_{\beta\theta}$, directly leading to values of $r_p$ and $C_\beta/C_\alpha$, can be solved numerically which allows the comparison with our experimental values for the patch size $r_p$ and contrast $C_\beta/C_\alpha$. These analytical solutions are obtained under the approximation that there is an infinite dilute reservoir with a constant supply $N_\alpha/N_{\alpha\theta} = Const = d$. This approximation is reasonable for our experimental condition, since $N_\alpha/N_{\alpha 0}$<0.1 and the relative change in $C_\alpha$ is less than 10%, even with the most enrichment condition.

As a result, the approximate solution to Equation (8) is:

$$\frac{N_\beta}{N_{\beta 0}} = \frac{2cd^2 + e^{a/b} - e^{\frac{a}{2b}}\sqrt{4cd^2 + e^{a/b}}}{2cd^2} \quad (10)$$

Where $\alpha = \Delta G_{DNA} - T\Delta S_r - kT$, $b = kT$, $c = A_w/A_{strep}$. This expression is directly linked to the measured patch intensity contrast $$C_\beta/C_\alpha = \frac{N_\beta}{N_{\beta 0}} \cdot \frac{N_{\alpha 0}}{N_\alpha} = \frac{N_\beta}{d \cdot N_{\beta 0}}.$$

Since we know the relation $N_{\beta 0} = \pi r_p^2/A_{strep}$, Equation (9) directly gives us:

$$r_p^2 = R^2 \frac{kT\left[2\ln\left(\frac{N_{\beta 0}}{N_{\beta 0} - N_\beta}\right) - \frac{N_\beta}{N_{\beta 0}}\right]}{\sigma A_{strep}} \quad (11)$$

$$\theta = \sqrt{\frac{kT\left[2\ln\left(\frac{N_{\beta 0}}{N_{\beta 0} - N_\beta}\right) - \frac{N_\beta}{N_{\beta 0}}\right]}{\sigma A_{strep}}} \quad (12)$$

We can now compare our experimental values to the ones found analytically here.

For the DNA sequence used in the experiments, $\Delta G_{DNA} = \Delta F_{DNA} - T\Delta S_{DNA}$ is $\approx -20$ kT at room temperature, and the experimental value for $T\Delta S_r$ are $-14.6$ kT for the double-stranded backbone DNA and $\sim 14.8$ kT for the single-stranded backbone one. We therefore use the same fitting parameters for both the ssb and dsb case. $A_w/A_{strep} \cong 34$ dsb while it is only $A_w/A_{strep} \cong 1$ for ssb DNA. This discrepancy is due to the different rigidities of the DNA strands: double stranded DNA is more rigid and rod-like and can thus reach a large number of strands on the opposite surface, whereas single stranded DNA behaves as a very exible polymer in our buffer conditions, with a persistent length of $\sim 2$ nm leading to a smaller end-to-end distance of $\approx 6$ nm, $\sigma \cong 15$ mN/m for phospholipid emulsions co-stabilized with 1 mM SDS. With a streptavidin size of $A_{strep} = 60$ nm$^2$ and the initial streptavidin surface concentration of $1400/\mu$m$^2$, this leads to $d_{min} \cong 0.09$.

Experimentally we vary the DNA surface density $d = N_{DNA}/N_{max}$ by changing the amount of DNA introduced in the system $N_{DNA} \sim 1$ pmol, 2 pmol, 4 pmol, 8 pmol, 20 pmol or 80 pmol. An ideal emulsion packing of 30 µL, as used in this experiment, can bind up to $N_{max} \sim 30$ pmol of DNA. Nevertheless the experiments require two washing steps of the emulsions before DNA conjugation, which is suspected to significantly reduce this number.

As a result, all the data in FIG. 8c and FIGS. 9b and 9c can be fitted with only two fitting parameters: $\Delta S_p = -16R$ and $N_{max} = 12$ pmol.

Polydisperse Emulsion Droplets Interaction

In the approximation of infinite reservoir, the only radius dependent term in the above set of equations are from the deformation energy. The deformation energy of the emulsions should be corrected as:

$$E_{deformation} = \frac{1}{4}\sigma\pi\frac{r_p^4}{R_1^2} + \frac{1}{4}\sigma\pi\frac{r_p^4}{R_2^2}$$

with different radius of contacting emulsions, R1 and R2, in the lowest order approximation. We define a square-averaged radius $$<R> = \sqrt{\frac{2R_1^2 R_2^2}{R_1^2 + R_2^2}},$$

so that $$E_{deformation} = \frac{1}{2}\sigma\pi\frac{r_p^4}{<R>^2}$$

and we can use all the equations in the previous section replacing R with <R>, as plotted or used in main text FIGS. 2c and d.

Linear Regression, Additional Geometry and Diffraction Limit

We fit $d_p$ as a function of <R> with a simple linear regression relation rather than a line $d_p = \theta R$ going through the origin as suggested by our model. The origin of this choice lies in geometrical arguments. Indeed the DNA constructs can be stretched, which leads to enrichment outside of the geometrically predicted adhesion patch. This additional area leads to a geometric factor $$\frac{\Delta L}{\theta}$$

contributing to me paten size. Both double-stranded and single-stranded DNA can extend up to $\Delta L \sim 12$ nm as estimated respectively from conventional teachings and a worm like chain model. This leads to an entropy loss of $\sim 2-3$ kT which reduces DNA concentration by half As a result the model is modified to include this additional term:

$$d_p = 2\theta R + \frac{\Delta L}{\theta} \quad (13)$$

The estimate for the respective intersections for dsb and ssb DNA give the values of $\Delta L/\theta \sim 80$ nm and $\sim 160$ nm, which are smaller than the experimental values of $\sim 150$ nm (dsb) and $\sim 210$ nm (ssb) that are certainly fixed by our experimental diffraction limit of $\sim 150$ nm.

Nevertheless, the fitting curves with either $$d_p = 2\theta R + \frac{\Delta L}{\theta} \text{ or } d_p = 2\theta R$$

are similar with the data shown in FIG. 2C and the fitting parameter $\Delta S_p$ only changes by $\sim 5\%$ to fit the data. Therefore the limits of our experimental accuracy do not allow us to discriminate between the two relationships.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of self-assembly to form end product, comprising the steps of:
   providing a first emulsion droplet for assembly;
   providing a second emulsion droplet for assembly;
   providing a first linker comprising a colloidal nanoparticle which can be coupled to the first emulsion droplet;
   forming a first patch, comprising the first linker, between the first emulsion droplet and the second emulsion droplet.

2. The method as defined in claim 1 wherein pseudo-bonding valency is established for the linker components.

3. The method as defined in claim 2 wherein a valency of 2 enables formation of flexible polymers of emulsion droplets.

4. The method as defined in claim 2 wherein a pseudo-valency of 4 enables formation of rigid polymer networks.

5. The method as defined in claim 1 wherein the first linker further comprises a plurality of single stranded DNA, attached to the colloidal nanoparticle, having a first sequence and further wherein the first emulsion droplet and the second emulsion droplet each have attached thereto a plurality of single stranded DNA having a second sequence, the second sequence and the first sequence being complementary.

6. The method as defined in claim 1 further including the step of mixing the end production with a personal care product matrix.

7. The method as defined in claim 1 further including the step of mixing the end product with a food product matrix.

8. The method as defined in claim 1 wherein the end production consists of an amorphous material having selectable rheological properties, thereby enabling processing of the end product to operate consumer products having desired properties.

9. The method as defined in claim 1 further including the step of cycling temperature of the end product.

10. The method as defined in claim 1 wherein the linker component comprises DNA strands further including the step of increased coverage of the DNA strands on the first component, thereby enabling tuning of reversibility of self-assembly.

11. A method of self-assembly to form end product, comprising the steps of:
    providing an emulsion having a plurality of emulsion droplets and a plurality of linkers, wherein each linker comprises a nanoparticle having attached thereto a first DNA strand and a second DNA strand and the concentration of the plurality of linkers is selected to provide a desired valency;
    providing a first linker and a second linker of the plurality of linkers, each of the first linker and the second linker engagable with the plurality of emulsion droplets and engageable with each other;
    engaging the first DNA strand with a first emulsion droplet of the plurality of droplets;
    engaging the second DNA strand with a second emulsion droplet of the plurality of droplets;
    forming a patch between the first emulsion droplet and the second emulsion droplet comprising the first DNA strand, the nanoparticle, and the second DNA strand;
    engaging the first emulsion droplet with additional emulsion droplets to achieve the desired valency and
    creaming the emulsion forming a floppy network of the plurality of emulsion droplets interconnected by a plurality of patches.

12. The method of claim 11, wherein the emulsion has a ratio of 5 to 1 of the plurality of linkers to the plurality of droplets, whereby a linear assembly is formed.

13. The method of claim 11, wherein the emulsion has a ratio of 100 to 1 of the plurality of linkers to the plurality of emulsion droplets, whereby a folded assembly is formed.

14. The method of claim 11, further comprising selecting a valency for the floppy network.

* * * * *

SEQUENCE LISTING

```
<160> NUMBER OF SEQ ID NOS: 5

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-BiotinTEG
<220> FEATURE:
<221> NAME/KEY: modified_base
<222> LOCATION: (1)..(49)
<223> OTHER INFORMATION: a, c, t, g, unknown or other

<400> SEQUENCE: 1
nnnnnnnnnn nnnnnnnnnn nnnnnnnnnn nnnnnnnnnn nnnnnnnnng gatgaagatg        60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-BiotinTEG
<220> FEATURE:
<221> NAME/KEY: modified_base
<222> LOCATION: (1)..(49)
<223> OTHER INFORMATION: a, c, t, g, unknown or other

<400> SEQUENCE: 2
nnnnnnnnnn nnnnnnnnnn nnnnnnnnnn nnnnnnnnnn nnnnnnnnnc atcttcatcc        60

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtaatgaa aggcagggct ctctggattg actgtgcgaa gggtagcgat                   50

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggatgaagat g                                                             11

<210> SEQ ID NO 5
<211> LENGTH: 11
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 5
catcttcatc c                                                           11
```